(12) United States Patent
McKay

(10) Patent No.: US 9,179,651 B2
(45) Date of Patent: Nov. 10, 2015

(54) SPECTROPHOTOMETRIC ANALYSIS OF EMBRYONIC CHICK FEATHER COLOR

(71) Applicant: MAT MALTA ADVANCED TECHNOLOGIES LIMITED, St. Julians (MT)

(72) Inventor: James C. McKay, Newbridge (GB)

( * ) Notice: Subject to any disclaimer, the term of this patent is extended or adjusted under 35 U.S.C. 154(b) by 0 days.

(21) Appl. No.: 14/011,439

(22) Filed: Aug. 27, 2013

(65) Prior Publication Data

US 2014/0069336 A1 Mar. 13, 2014

Related U.S. Application Data

(60) Provisional application No. 61/695,453, filed on Aug. 31, 2012.

(51) Int. Cl.
*G01N 33/08* (2006.01)
*A01K 43/00* (2006.01)
(Continued)

(52) U.S. Cl.
CPC .............. *A01K 43/00* (2013.01); *A01K 45/00* (2013.01); *G01N 21/49* (2013.01); *G01N 33/08* (2013.01)

(58) Field of Classification Search
CPC ....... A01K 43/00; A01K 43/04; A01K 43/10; A01K 45/00; A01K 45/007; G01N 33/08; G01N 21/49
USPC ..................................... 119/6.8, 174; 356/52
See application file for complete search history.

(56) References Cited

U.S. PATENT DOCUMENTS 4,161,366 A 7/1979 Bol et al.
4,182,571 A 1/1980 Furuta et al.
(Continued)

FOREIGN PATENT DOCUMENTS

DE 102007013107 A1 * 9/2008 ............. G01N 21/65
WO 2010150265 A2 12/2010
(Continued)

OTHER PUBLICATIONS

Smith et al., Detection of hatching and table egg defects using hyperspectral imaging, USDA (2006), available at http://www.researchgate.net/publication/228820808_Detection_of_hatching_and_table_egg_defects_using_hyperspectral_imaging.*
(Continued)

*Primary Examiner* — Lisa Tsang
(74) *Attorney, Agent, or Firm* — Jeremy A. Smith; Stephen H. Hall; Bradley Arant Boult Cummings LLP

(57) ABSTRACT

In one embodiment, a process and method of screening an avian embryo feather color (pre-hatching) and determining the sex of the avian embryo, based at least in part, on the feather color or the color of feather precursors is provided. In an alternate embodiment, a process and method of screening chick embryo sex is provided, comprising the steps of: (i) obtaining a chicken egg; (ii) exposing the chicken egg to, or contacting the chicken egg with, electromagnetic radiation emitted from an electromagnetic radiation source; (iii) determining the amount of absorption, diffusion, refraction, reflection or a combination of any of the forgoing, of the electromagnetic radiation by the chicken egg by using an imaging system; (iv) comparing the absorption, diffusion, refraction, reflection or a combination of any of the forgoing, of the electromagnetic radiation by the chicken egg to a database; and (v) determining the sex of the chick embryo in the chicken egg, at least in part, as a result of the comparing step.

18 Claims, 3 Drawing Sheets

(51) Int. Cl.
*A01K 45/00* (2006.01)
*G01N 21/49* (2006.01)

(56) References Cited

U.S. PATENT DOCUMENTS

| | | | |
|---|---|---|---|
| 4,788,427 A | 11/1988 | LeRoy | |
| 4,914,672 A | 4/1990 | Hebrank | |
| 4,955,728 A | 9/1990 | Hebrank | |
| 5,173,737 A | 12/1992 | Mitchell et al. | |
| 5,575,237 A * | 11/1996 | Ferguson | 119/6.8 |
| 5,745,228 A | 4/1998 | Hebrank et al. | |
| 6,029,080 A | 2/2000 | Reynnells et al. | |
| 6,373,560 B1 | 4/2002 | Roux | |
| 6,396,938 B1 * | 5/2002 | Tao et al. | 382/110 |
| 6,535,277 B2 | 3/2003 | Chalker, II et al. | |
| 6,750,954 B2 | 6/2004 | Hebrank et al. | |
| 6,860,225 B2 | 3/2005 | Hebrank | |
| 7,019,821 B2 | 3/2006 | Kageyama et al. | |
| 7,154,594 B2 | 12/2006 | Reeves et al. | |
| 7,289,196 B2 | 10/2007 | Reeves et al. | |
| 7,336,348 B2 | 2/2008 | Reeves et al. | |
| 7,950,349 B1 * | 5/2011 | Rollins | 119/6.8 |
| 8,624,190 B2 * | 1/2014 | Steiner et al. | 250/339.08 |
| 2007/0024844 A1 * | 2/2007 | Hebrank et al. | 356/53 |
| 2011/0144473 A1 | 6/2011 | Opitz et al. | |
| 2012/0058052 A1 | 3/2012 | Decuypere et al. | |
| 2013/0044210 A1 | 2/2013 | Rozenboim et al. | |

FOREIGN PATENT DOCUMENTS

| | | |
|---|---|---|
| WO | PCT/IL2010/000512 | 12/2010 |
| WO | WO 2010150265 A2 | 12/2010 |

OTHER PUBLICATIONS

English-language translation of DE 10 2007 013107 A1.*
D.P. Smith et al., Fertility and Embryo Development of Broiler Hatching Eggs Evaluated with a Hyperspectral Imaging and Predictive Modeling System, International J. of Poultry Science, 2008, vol. 7, No. 10, pp. 1001-1004, USA.
A. Giunchi et al., Non-destructive Freshness Assessment of Sheel Eggs using FT-NIR Spectroscopy, J. of Food Engineering, Nov. 2008, vol. 89, No. 2, pp. 142-148.
K. Lawrence et al., Egg Embryo Detection with Hypersectral Imaging, Poultry Science, 2006, vol. 5, p. 964.
Morgan, T.H.; Heredity and Sex; 1913; Columbia University Press; New York, United States.
Steiner, G., Bartels, T., Stelling, A., Krautwald-Junghanns, M.E., Fuhrmann, H., Sablinskas, V., & Koch, E.; Gender determination of fertilized unincubated chicken eggs by infrared spectroscopic imaging; Anal Bioanal Chem (2011) 400:2775-2782; Apr. 9, 2011; Springer-Verlag; Germany.
Mingke Yu, Zhicao Yue, Ping Wu, Da-Yu Wu, Julie-Ann Mayer, Marcus Medina, Randall B. Widelitz, Ting-Xin Jiang, & Cheng-Ming Chuong; The developmental biology of feather follicles; Int. J. Dev. Biol. 48: 181-191 (2004); Spain.
Smith, T.W.; Avian Embryo; Mississippi State University; United States.
Smith, D.P., Lawrence K.C., Heitschmidt, G.W.; Fertility and embryo development of broiler hatching eggs evaluated with a hyperspectral imaging and predictive modeling system; International Journal of Poultry Science 7 (10): 1001-1004, 2008; United States.
Lawrence K.C., Smith, D.P., Windham, W.R., Heitschmidt, G.W., Park, B.; Egg embryo development detection with hyperspectral imaging; International Journal of Poultry Science 5 (10): 964-969, 2006, United States.
International Search Report (ISR) for PCT/IB2013/002400 issued on Thursday, Mar. 12, 2015 by the International Bureau.

* cited by examiner

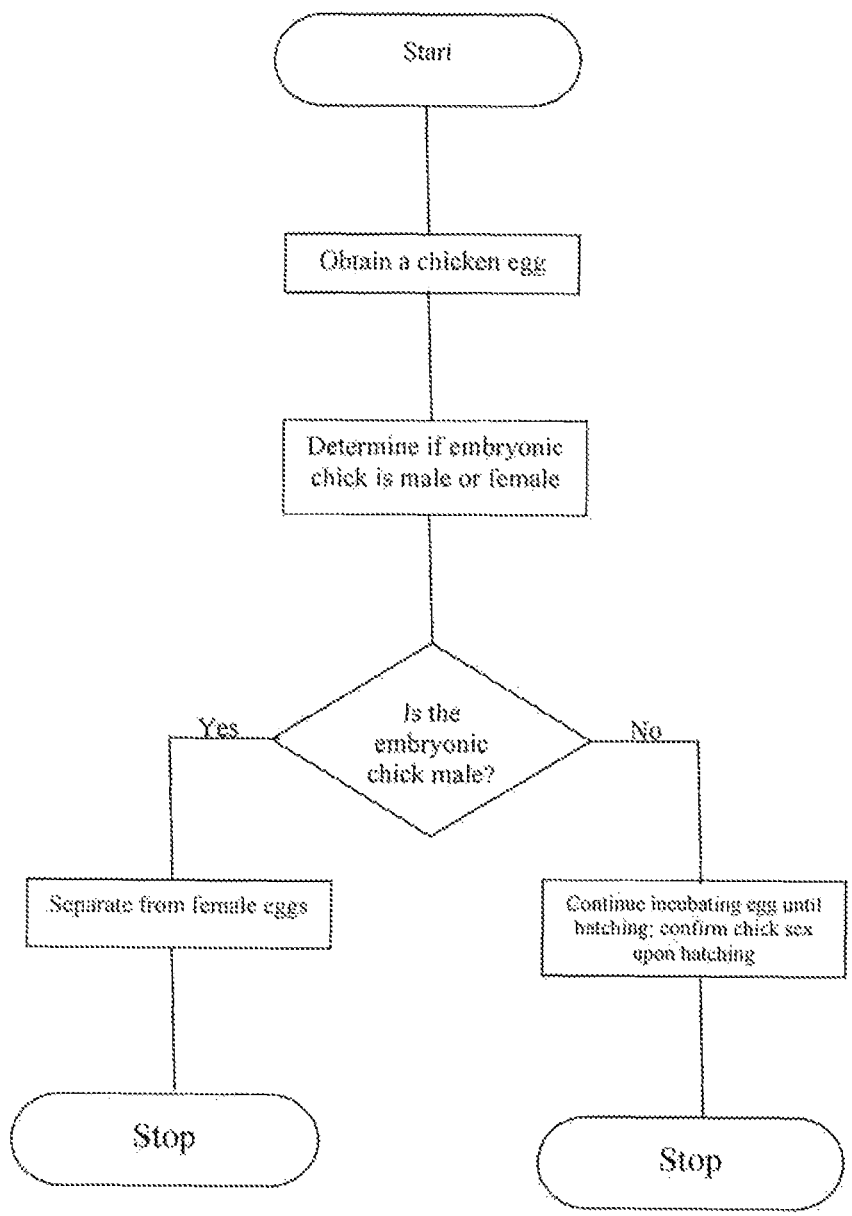

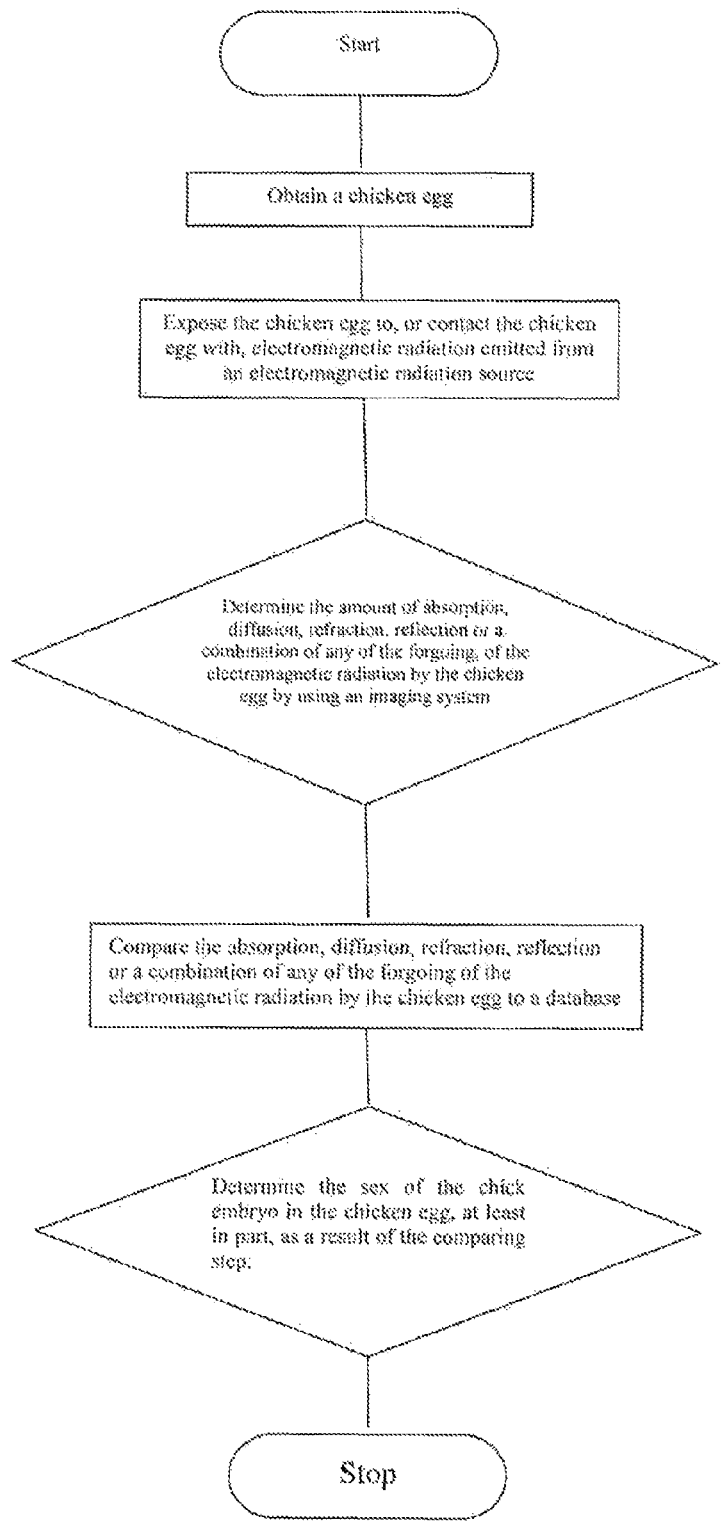

SPECTROPHOTOMETRIC ANALYSIS OF EMBRYONIC CHICK FEATHER COLOR

CROSS REFERENCE TO OTHER APPLICATIONS

This application is a continuation of, and claims the benefit of and priority to, U.S. Provisional Application No. 61/695,453 filed Aug. 31, 2012 entitled "Spectrophotometric Analysis of Embryonic Chick Feather Color."

FIELD OF THE INVENTION

The invention relates generally to the determination of the feather color of an avian embryo and determining the sex of the embryo based, at least in part, upon the feather color.

BACKGROUND ART

In 2006, the United States produced more than 12 billion (12,000,000,000) chicken eggs. In the egg production industry, only the female chicks are productive and the male chicks are currently culled. The culling of male chicks typically occurs after hatching and presents serious problems both economically and ethically. Economically, culling the male chicks is labor intensive and requires that certain waste disposal guidelines be followed. Ethically, the large scale culling of male chicks is undesirable to the industry consumers and the general public.

While there are a number of known methods useful to screen or determine the sex of many avian species, both pre- and post-hatching, the known methods fall short for several reasons. For simplicity, much of the specification will refer to known methods, and the present invention, as they relate to determination of the sex of a chick. However, many of the known methods can be used to determine the sex of other avian species, and the novel system and methods disclosed herein can similarly be utilized for avian species other than chickens. For example, the known pre-hatch screening methods are in some cases unreliable and are only available relatively late in the twenty one (21) day developmental cycle of the chick embryo. Many of the known pre-hatch screening methods analyze chick sex only after day eleven (11) in development which is after the point of development that the chick embryo is considered a sentient animal.

Thus the known pre-hatch screening methods do not avoid the ethical issues associated with post-hatch sexing. Second, many of the current pre-hatch methods are invasive and require sampling the contents of the egg, often by penetrating, or creating a hole in, the egg shell, thus compromising egg quality, embryo survival, physically damaging the egg and potentially introducing a source of contamination. The samples taken from the egg then require cost and time, or intensive assays of DNA, hormones or other metabolites to determine sex.

The known post-hatch sexing methods suffer many of the same drawbacks and limitations as discussed above and require extensive labor and expense or present waste disposal and ethical issues. One wide spread method of determining chick sex after hatching is feather color differentiation, designated on FIG. 1 as "$fc$". Feathers are elaborate skin appendages that serve many functions on a bird, including communication, regulation of body temperature and in some species, flight. Feathers originate from feather follicles and in the modern chicken, beginning on the $8^{th}$ day of incubation, feathers have begun to form, and they are readily apparent on the $10^{th}$ day of incubation. Further, feather color or pigmentation exists by the $10^{th}$ day of incubation, as shown in FIG. 1. Feather color is determined by the expression of certain pigments by the cells forming the feather/feather precursor. Using feather color differentiation $fc$ to sex newly hatched chicks was developed over a century ago, and today, commercial breeds of chickens (as well as some wild type breeds) can be sexed at over 99% accuracy based upon feather color after hatching. One common color scheme used in feather color differentiation $fc$ involves breeding chickens with a sex-linked genetic marker so that male chicks are born with brown feathers while female chicks are born with white feathers, or vice versa. As shown in FIG. 1 as an example of developing brown feathers in a female chick embryo, the differentiation of feather color $fc$ may exist as early as days 8-10 of egg incubation in some breeds of chickens and persists to hatching.

Accordingly, it is desirable that a method and apparatus be developed that allows for the non-invasive embryonic (or pre-hatch) determination of chick sex using feather color.

The unmet needs described above, as well as others are addressed by various embodiments of the methods, systems, and devices provided by the present application; although it is to be understood that not every embodiment disclosed will address a given need.

SUMMARY OF THE INVENTION

In some aspects, the invention relates to a process and method of screening an avian embryo feather color (pre-hatching) and determining the sex of the avian embryo, based at least in part, on the feather color or the color of feather precursors.

In other aspects, the invention relates to a method of screening chick embryo sex, the method comprising the steps of: (i) obtaining a chicken egg; (ii) exposing the chicken egg to, or contacting the chicken egg with, electromagnetic radiation emitted from an electromagnetic radiation source; (iii) determining the amount of absorption, diffusion, refraction, reflection or a combination of any of the forgoing, of the electromagnetic radiation by the chicken egg by using an imaging system; (iv) comparing the absorption, diffusion, refraction, reflection or a combination of any of the forgoing of the electromagnetic radiation by the chicken egg to a database; and (v) determining the sex of the chick embryo in the chicken egg, at least in part, as a result of the comparing step.

Other aspects and advantages of the invention will be apparent from the following description and the appended claims and drawings.

BRIEF DESCRIPTION OF DRAWINGS

To further the advantages and features of the present application, a more particular description of the invention will be rendered by reference to specific embodiments thereof which are illustrated in the appended drawings. It should be noted that identical features in different drawings are shown with the same reference numeral. It is appreciated that these drawings are not to be considered limiting in scope. The invention will be described and explained with additional specificity and detail through the use of the accompanying drawings in which:

FIG. 2 shows a flowchart diagram of one embodiment of screening embryonic chicks disclosed by the present application.

FIG. 3 shows a more detailed flowchart diagram of one embodiment of screening embryonic chicks disclosed by the present application.

DETAILED DESCRIPTION

A. Definitions

Figure 1:
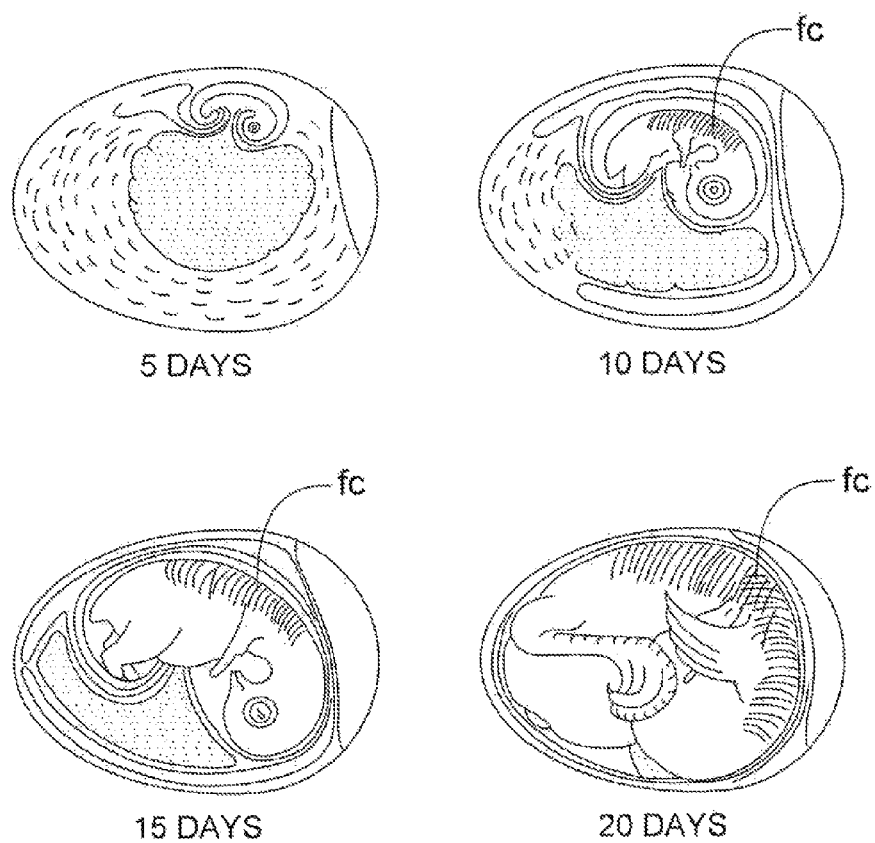
FIG. 1 shows the stages of embryonic development of a male chicken embryo with the feather color differentiation $fc$ existing on day 10 of development.

With reference to the use of the word(s) "comprise" or "comprises" or "comprising" in the following description and claims, unless the context requires otherwise, those words are used on the basis and clear understanding that they are to be interpreted inclusively, rather than exclusively, and that each of those words is to be so interpreted.

The term "about" as used herein refers to a value that may vary within the range of expected error inherent in typical measurement techniques known in the art.

The term "storage device" as used herein refers to a machine-readable device that retains data that can be read by mechanical, optical, or electronic means, for example by a computer. Such devices are sometimes referred to as "memory," although as used herein a machine-readable data storage device cannot comprise a human mind, in whole or in part, including human memory. A storage device may be classified as primary, secondary, tertiary, or off-line storage. Examples of a storage device that is primary storage include the register of a central processing unit, the cache of a central processing unit, and random-access memory (RAM) that is accessible to a central processing unit via a memory bus (generally comprising an address bus and a data bus). Primary storage is generally volatile memory, which has the advantage of being rapidly accessible. A storage device that is secondary storage is not directly accessible to the central processing unit, but is accessible to the central processing unit via an input/output channel. Examples of a storage device that is secondary storage include a mass storage device, such as a magnetic hard disk, an optical disk, a drum drive, flash memory, a floppy disk, a magnetic tape, an optical tape, a paper tape, and a plurality of punch cards. A storage device that is tertiary storage is not connected to the central processing unit until it is needed, generally accessed robotically. Examples of a storage device that is tertiary storage may be any storage device that is suitable for secondary storage, but configured such that it is not constantly connected to the central processing unit. A storage device that is off-line storage is not connected to the central processing unit, and does not become so connected without human intervention. Examples of a storage device that is off-line storage may be any storage device that is suitable for secondary storage, but configured such that it is not constantly connected to the central processing unit, and does not become so connected without human intervention. Secondary, tertiary, and offline storage are generally non-volatile, which has the advantage of requiring no source of electrical current to maintain the recorded information. A storage device cannot be construed to be a mere signal, although information may be communicated to and from a storage device via a signal.

The term "processor" or "central processing unit" (CPU) as used herein refers to a software execution device capable of executing a sequence of instructions ("program"). The CPU comprises an arithmetic logic unit, and may further comprise one or both of a register and cache memory.

The term "machine-readable format" as used herein refers to a medium of storing information that is configured to be read by a machine or processor. Such formats include magnetic media, optical media, and paper media (punch cards, paper tape, etc.). Printed writing in a human language, if not intended or configured to be read by a machine, is not considered a machine readable format. In no case shall a human mind be construed as "machine readable format."

The term "database" as used herein refers to an organized data structure comprising a plurality of records stored in machine-readable format.

B. Methods/Processes

The present application provides a process and method of screening avian embryo feather color (pre-hatching) and determining the sex of the avian embryo, based at least in part, on the feather color or the color of feather precursors. In one embodiment, the present application provides a process and method for the pre-hatch screening of chick sex.

In one embodiment, as illustrated in FIGS. 2 and 3, determining the sex of the chick embryo allows for the better utilization of resources in that the less desirable male embryos can be separated and the more desirable female embryos can continue incubation until hatching.

In one embodiment, the method comprises the steps of: (i) obtaining a chicken egg; (ii) exposing the chicken egg to, or contacting the chicken egg with, electromagnetic radiation emitted from an electromagnetic radiation source; (iii) determining the amount of absorption, diffusion, refraction, reflection or a combination of any of the forgoing, of the electromagnetic radiation by the chicken egg by using an imaging system: (iv) comparing the absorption, diffusion, refraction, reflection or a combination of any of the forgoing of the electromagnetic radiation by the chicken egg to a database; and (v) determining the sex of the chick embryo in the chicken egg, at least in part, as a result of the comparing step.

1. Obtaining the Chicken Egg.

In one embodiment, the chicken egg is an egg that is believed to be fertilized or that is known to be fertilized and may have been incubated for a period of time after laying. In one embodiment, the egg has been incubated for about 5-15 days before being screened. In an alternate embodiment, the egg has been incubated for about 7-13 days before being screened. In another embodiment, the egg has being incubated for about 9-11 days before being screened. In yet another alternate embodiment, the egg has been incubated for about 10 days before being screened. The egg may be incubated under appropriate conditions for sufficient or optimal embryonic growth and is well known in the industry. In one embodiment the eggs may be incubated at about 37.6 degrees Celsius and in about 56-62% relative humidity for the first eighteen (18) days of incubation and at about 37.4 degrees Celsius and in about 70-83% relative humidity for the last three (3) days of incubation. Those of ordinary skill in the art will recognize that incubation conditions of an egg may vary slightly over time, from breed-to-breed and between species. Such known incubation conditions and variations should be considered within the scope of the present disclosure.

In one embodiment, the chicken egg is obtained from a breed of chicken that produces feather color differentiation in chicks based upon the sex of the chick. For example, in one embodiment, the chicken may produce female chicks with brown feathers while male chicks have white feathers, or vice versa. In one embodiment, the chicken lines used as breeding stock ("Parent Stock") differ at a sex-linked genetic marker locus conferring brown feathering in the male line and white feathering in the female line. When a Parent Stock cross is made involving males of the brown line and females of the white line, the commercial generation progeny may be sexed by the resulting color differentiation, the females being brown and the males white. Other genetic markers may be available in different breeds or species. These other genetic markers which produce sex linked differences in gene expression or sex-limited gene expression may be used in accordance with the methods and systems disclosed herein.

2. Exposing the Chicken Egg to, or Contacting the Chicken Egg with, Electromagnetic Radiation.

In one embodiment, the method comprises contacting the chicken egg with, or exposing the chicken egg to, electromagnetic radiation. The electromagnetic radiation is typically created from the emission and propagation of electromagnetic waves. In one embodiment, the electromagnetic radiation ranges a spectrum of wavelengths from about $10^{-11}$ meters to about $10^3$ meters. The electromagnetic radiation may be emitted from any suitable electromagnetic radiation source. In one embodiment, the electromagnetic radiation source is a light bulb, such as a tungsten-halogen light bulb (though any other light source capable of producing the desired wavelength of electromagnetic radiation can be used). Emission sources of electromagnetic radiation are well known in the art and those of ordinary skill in the art could select the appropriate emission source based upon the desired wavelength(s) of electromagnetic radiation to be used and such known emission sources should be considered within the scope of this disclosure.

In one embodiment, the emission source may comprise part of an hyperspectral imaging system (described in more detail below) such as the systems disclosed by K. C. Lawrence et al., Int'l J. of Poultry Sci., 5(10): 964-969 (2006) or D. P. Smith et al., Int'l J. of Poultry Sci., 7(10): 1001-1004 (2008). Applicant hereby incorporates the teachings and disclosures of the preceding references into the present application. In an alternate embodiment, emission source may comprise part of a commercially available hyperspectral imaging system, which may be used to determine an average value $\alpha v$ as discussed herein.

In one embodiment, only one emission source may be used. The emission source may be placed at various angles relative to the egg being screened. In one embodiment, the single emission source may be placed anywhere on a three hundred and sixty (360) degree circle that surrounds the egg being screened. In one embodiment, the emission source may be stationary at a ninety (90) degree angle relative to the chicken egg (either directly to the side, above or below) while in an alternate embodiment the stationary emission source may be at a forty (45) degree angle to the chicken egg. Of course, a number of emission source locations at various positions relative to the egg being screened could be used to obtain the desired exposure to, or contact with, the electromagnetic radiation. In an alternate embodiment, the single emission source may be adapted to be moveable relative to the chicken egg such that the single emission source may be adapted to be moved by a robotic arm or other processor controlled means. Additionally, in other embodiments, the chicken egg may be moved while the single emission source remains stationary. Those of ordinary skill in the art will recognize that there are many methods and devices capable of moving the single emission source or the egg relative to one another, and such methods and devices should be considered within the scope of this disclosure. In one embodiment, the single emission source may be used to generate several images of the egg from different angles.

In an alternate embodiment, there may be a plurality of emission sources used. In an embodiment where there are a plurality of emission sources, the emission sources may be placed anywhere on a three hundred and sixty (360) degree circle that surrounds the egg being screened. In one embodiment, the one emission source may be located at a ninety (90) degree angle relative to the chicken egg (either directly to the side, above or below) while a second emission source may be at a forty (45) degree angle to the chicken egg. Of course, a number of emission sources located at various positions relative to the egg being screened could be used to obtain the desired exposure to, or contact with, the electromagnetic radiation. In an alternate embodiment, the plurality of emission sources may be adapted to be moveable relative to the chicken egg such that the emission sources may be adapted to be moved by a robotic arm or other processor controlled means. Additionally, in other embodiments, the chicken egg may be moved while the emission sources remain stationary. Those of ordinary skill in the art will recognize that there are many methods and devices capable of moving the emission sources or the egg relative to one another, and such methods and devices should be considered within the scope of this disclosure.

In one embodiment, the electromagnetic radiation ranges from a wavelength of about 0.01 nm to 1,000,000 nm. In another embodiment, the electromagnetic radiation ranges from a wavelength of about 0.01 nm to 10 nm. In another embodiment, the electromagnetic radiation ranges from a wavelength of about 10 nm to 380 nm. In another embodiment, the electromagnetic radiation ranges from a wavelength of about 380 nm to 740 nm. In yet another embodiment, the electromagnetic radiation ranges from a wavelength of about 750 nm to 1,000 nm. In one embodiment, the electromagnetic radiation may be a combination of the forgoing wavelengths, including a plurality of wavelengths from about 10 nm to 1,000 nm.

3. Determining the Amount of Absorption, Diffusion or Refraction of the Electromagnetic Radiation by the Chicken Egg.

After the chicken egg is contacted with, or exposed to, the electromagnetic radiation, a certain amount of the electromagnetic radiation will either be absorbed, diffused, reflected or refracted (or perhaps a combination of any of the forgoing) by the egg and the contents inside of the egg.

In one embodiment, the absorption of the electromagnetic radiation may be determined by employing devices and methods known to those of ordinary skill in the art, and such devices should be considered within the scope of this disclosure.

In one embodiment, the diffusion of the electromagnetic radiation may be determined by employing devices and methods known to those of ordinary skill in the art, and such devices should be considered within the scope of this disclosure.

In one embodiment, the reflection of the electromagnetic radiation may be determined by employing devices and methods known to those of ordinary skill in the art, and such devices should be considered within the scope of this disclosure.

In one embodiment, the refraction of the electromagnetic radiation may be determined by employing devices and methods known to those of ordinary skill in the art, and such devices should be considered within the scope of this disclosure.

In one embodiment, the absorption, diffusion, reflection, refraction, or a combination of any or all of the forgoing, of the electromagnetic radiation is used to determine, at least in part, chick sex.

In one further embodiment, the absorption, diffusion, reflection or refraction of the electromagnetic radiation is determined, at least in part, by the utilization of a spectrohotometric or hyperspectral imaging system, such as those that are known to one of ordinary skill in the art and those known imaging systems should be considered within the scope of this disclosure. In one embodiment, the spectrohotometric imaging system comprises a camera (or other device), which captures or records the spectral and/or spatial images of the chicken eggs, any necessary lenses and a processor. In one embodiment, the absorption, diffusion, reflection or refraction of the electromagnetic radiation of the egg may be determined using a hyperspectral imaging system such as the systems disclosed by K. C. Lawrence et al., infra or D. P. Smith et al., infra. In an alternate embodiment, the camera may be a Verde Hyperspectral Camera available from Horiba Scientific.

After capturing or recording the image, the image may be acted upon, or read by, a processor and in some embodiments, an associated storage device, to determine a value v that corresponds, at least in part, to the absorption, diffusion, reflection or refraction (or a combination of any of the forgoing) of electromagnetic radiation by the egg. This value v may be determined by any method known to one of ordinary skill in the art and such methods of determination should be considered within the scope of this disclosure. In one embodiment, value v may be determined by calculating the percentage of absorption of the electromagnetic radiation (of one or a plurality of wavelengths) of the egg being screened. In an alternate embodiment, the value v may be determined by calculating a number of other factors in addition to the absorption of the electromagnetic radiation using methods such as principal factor analysis or other similar methods. In one embodiment, calculation of value v may be improved during the practice of the method through incorporating results from post-hatch confirmation of the egg being screened. The value v will be influenced, at least in part, by the presence or absence of brown feathers, feather precursors or pigments in either of the forgoing on the embryonic chick. In particular a female embryonic chick with brown feathers, feather precursors, and/or pigments will produce a different value v than a male embryonic chick without brown feathers, feather precursors or pigments (and vice versa) in either of the forgoing.

In some embodiments, the value v may be determined by capturing or recording only one image of the egg, while in other embodiments a plurality of images of the egg may be captured or recorded. In some embodiments, the images to be captured or recorded may be generated from a single electromagnetic radiation source while in other embodiments a plurality of emission sources may be used. It is believed that capturing or recording multiple images of an egg may reduce background noise or other issues that reduce the quality of one image and therefore that a plurality images may be desirable. In the embodiment where a plurality of images for an egg are captured or recorded, an average value αv may be calculated by a processor by calculating the average of all values v associated with each image of the egg and in other embodiments, statistical analysis may be employed by the processor to ignore certain outlier values v.

4. Comparing the Absorption, Diffusion, Retraction of the Forgoing of the Electromagnetic Radiation by the Chicken Egg to a Database and Determining the Sex of the Chick Embryo in the Chicken Egg as a Result of the Comparing Step.

In some embodiments, after the value v or the average value αv for a particular egg is determined, value v or the average value may be compared by a processor, and possibly an associated storage device, to a database comprising one or more standard values sv. In one embodiment, the standard values sv may have been previously determined through gathering data concerning the absorption, diffusion, reflection or refraction of electromagnetic radiation by a population of eggs and correlating that data to chick sex after hatching. In one embodiment value v, average value αv and standard value sv may be a range rather than an exact number. For examples, an average value αv in a certain range may correlate to a determination that the egg being screened comprises a male embryo. After the value v or the average value αv is compared to the standard value sv to determine whether the embryonic chick is male or female, based upon, at least in part, the presence or absence of brown feathers, feather precursors or pigment.

Once embryonic sex is determined, the female embryos may be allowed to continue incubating until hatching while the male embryos may be separated for other uses or culled.

In other embodiments, the methods disclosed herein may be useful for sexing pre-hatched avian embryos of other species, including but not limited to turkeys and ducks.

C. Conclusion

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present application. Additionally, the application shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present application are not intended to limit the exact embodiments and examples disclosed herein. Any section headings herein are provided only for consistency with the suggestions of 37 C.F.R. §1.77 or otherwise to provide organizational queues. These headings shall not limit or characterize the invention(s) set forth herein.

What is claimed is:

1. A method of non-invasive embryonic determination of avian sex, the method comprising the steps of:
   (a) producing a training set of avian eggs from an avian strain cross designed to produce a sex-related difference in feather colour having feather colour differentiation genetic characteristics;
   (b) exposing the training set of avian eggs to electromagnetic energy comprising a plurality of different wavelengths of between about 380 nm and 740 nm, wherein the training set of avian eggs has been incubated for a period of time less than 14 days;

(c) determining an amount of absorption, diffusion, refraction, reflection, or a combination of any of the forgoing, the electromagnetic energy for each of the plurality of different wavelengths of each avian egg in the training set of avian eggs, the amount caused by the feather colour differentiation genetic characteristics;

(d) determining the sex of embryos or avians of the training set of avian eggs;

(e) correlating the amount determined in step (c) to the sex determined in step (d);

(f) determining standard value ranges of the amounts determined in step (c) that are indicative of the sex of the avian egg from an avian breed having the feather colour differentiation genetic characteristics, wherein a standard value range is determined for males at each of said plurality of wavelengths and a standard value range is determined for females at each of said plurality of wavelengths;

(g) storing said standard value ranges in a database;

(h) exposing a test set of avian eggs from the same avian breed as the training set of avian eggs to electromagnetic energy comprising the same plurality of wavelengths used on the training set of avian eggs, wherein the test set of avian eggs has been incubated for a period of time less than 14 days; and (i) determining an amount of absorption, diffusion, refraction, reflection, or a combination of any of the forgoing, of the electromagnetic energy for each of the plurality of different wavelengths by the test set of avian eggs, (j) comparing the amount determined in step (i) to the standard value ranges stored in the database to determine the sex of each egg in the test set of avian eggs; and (k) culling the avian eggs determined to be male in the comparing step.

2. A method of sexing embryonic chicks, the method comprising the steps of:

a. exposing a chicken egg from an chicken breed having feather colour differentiation genetic characteristics to, or contacting the chicken egg with, electromagnetic radiation at a plurality of different wavelengths emitted from an electromagnetic radiation source;

b. determining an amount of absorption, diffusion, refraction, reflection, or a combination of any of the forgoing, of the electromagnetic radiation for each of the plurality of different wavelengths by the chicken egg, the amount at least in part caused by feather colour differentiation genetic characteristic;

c. comparing the absorption, diffusion, refraction, reflection or a combination of any of the forgoing of the electromagnetic radiation by the chicken egg to a database of standard value ranges indicative of an amount of absorption, diffusion, refraction, reflection, or any combination of any of the foregoing, by eggs containing male embryos and eggs containing female embryos of a training population of chicken eggs from the same said chicken breed having the feather colour differentiation genetic characteristics, wherein the standard value ranges are derived by (i) exposing a training population to electromagnetic radiation at the same said plurality of different wavelengths; (ii) determining an amount of absorption, diffusion, refraction, reflection, or a combination of any of the foregoing, of the electromagnetic radiation for each of the plurality of wavelengths caused by the feather colour differentiation characteristic, and (iii) correlating the determined amount of absorption, diffusion, refraction, reflection, or a combination of any of the foregoing, of the electromagnetic radiation for each of the plurality of different wavelengths to the sex of eggs of the training population; and d. determining a sex of a chick embryo in the chicken egg, at least in part, as a result of the comparing step.

3. The method of claim 2 wherein the chicken egg has been incubated for a period of time about 5-15 days after laying.

4. The method of claim 3 wherein the chicken egg has been incubated for a period of time of about 9-11 days after laying.

5. The method of claim 2 wherein the electromagnetic radiation comprises a plurality of different wave lengths of between about 10 nm and about 1,000 nm.

6. The method of claim 2 wherein the electromagnetic radiation comprises a plurality of different wave lengths of between about 380 nm and 740 nm.

7. The method of claim 2 wherein the electromagnetic radiation comprises a plurality of wavelengths from about 650 nm to 1,000 nm.

8. The method of claim 2 further comprising a plurality of electromagnetic radiation sources, wherein each electromagnetic radiation source is placed in a unique position relative to the chicken egg.

9. The method of claim 2 wherein the absorption, diffusion, refraction, reflection, or a combination of any of the forgoing, of the electromagnetic radiation by the chicken egg is determined, at least in part, by presence or absence of brown feathers or feather precursors on the chicken embryo inside of the chicken egg.

10. The method of claim 2 wherein the absorption, diffusion, refraction, reflection, or a combination of any of the forgoing, of the electromagnetic radiation by the chicken egg is determined, at least in part, by presence or absence of brown pigment inside of the chicken egg.

11. The method of claim 2 wherein the amount of absorption, diffusion, refraction, reflection, or a combination of any of the forgoing, of the electromagnetic radiation by the chicken egg is determined using a hyperspectral imaging system.

12. The method of claim 2 wherein the amount of absorption, diffusion, refraction, reflection, or a combination of any of the forgoing, of the electromagnetic radiation by the chicken egg is determined by capturing multiple images of the chicken egg and averaging the amount of absorption, diffusion, refraction, reflection, or a combination of any of the forgoing, indicated by each image.

13. A method of sexing avian embryos, the method comprising the steps of:

a. exposing an avian egg from an avian breed having feather colour differentiation genetic characteristics to, or contacting the egg with, electromagnetic radiation emitted from an electromagnetic, radiation source;

b. determining an amount of absorption, diffusion, refraction, reflection or a combination of any of the forgoing, of the electromagnetic radiation by the egg, wherein the absorption, diffusion, refraction, reflection or a combination of any of the forgoing, is determined, at least in part, by presence or absence of brown feathers or feather precursors inside of the egg;

c. comparing the absorption, diffusion, refraction, reflection, or a combination of any of the forgoing of the electromagnetic radiation by the egg to a pre-constructed database of standard values indicative of an amount of absorption, diffusion, refraction, reflection, or any combination of any of the foregoing, by male avian eggs and female avian eggs of a training population of avian eggs from the same said avian breed having the feather colour differentiation genetic characteristics, wherein said pre-constructed database comprises standard values derived by (i) exposing the training population to electromagnetic radiation; (ii) determining the amount of absorption, diffusion, refraction, reflection, or a combination of any of the forgoing of electromagnetic radiation by the training population eggs caused by the feather colour differentiation characteristic and (iii) correlating the determined amount of absorption, diffusion, refraction, reflection, or a combination of any of the foregoing, of the electromagnetic radiation by the training population eggs to a sex of the avian embryo of the training population after hatching by the presence or absence of brown feathers; and d. determining the sex of the avian embryo in the egg, at least in part, as a result of the comparing step.

14. The method of claim 13 wherein the avian egg has been incubated for a period of time about 5-15 days after laying.

15. The method of claim 14 wherein the avian egg has been incubated for a period of time of about 9-11 days after laying.

16. The method of claim 13 wherein the electromagnetic radiation comprises a wave length of between about 10 nm and about 1,000 nm.

17. The method of claim 13 wherein the electromagnetic radiation comprises a wave length of between about 380 nm and 740 nm.

18. The method of claim 13 wherein the electromagnetic radiation comprises a plurality of wavelengths from about 10 nm to 1,000 nm.

* * * * *